United States Patent [19]

Schumaier

[11] Patent Number: 5,640,783
[45] Date of Patent: Jun. 24, 1997

[54] HEARING AID DRYING APPLIANCE

[76] Inventor: Daniel R. Schumaier, Rte. 2, Elizabethton, Tenn. 37643

[21] Appl. No.: 427,804

[22] Filed: Apr. 26, 1995

[51] Int. Cl.$^6$ ................................................. F26B 19/00
[52] U.S. Cl. ................................. 34/219; 34/80; 34/225
[58] Field of Search ................................. 34/80, 81, 78, 34/219, 225, 472, 473

[56] References Cited

U.S. PATENT DOCUMENTS

| | | | |
|---|---|---|---|
| 2,913,832 | 11/1959 | Kaufman | 34/80 |
| 3,270,428 | 9/1966 | Van Olphen | 34/80 |
| 4,471,537 | 9/1984 | Meda | 34/225 |
| 5,048,201 | 9/1991 | Layton | 34/80 |
| 5,152,077 | 10/1992 | Liang | 34/219 |

Primary Examiner—John T. Kwon

[57] ABSTRACT

A dryer appliance for demoisturizing a moisture sensitive item such as an electronic hearing aid or the like, having a housing with a removable cap for providing a substantially sealed chamber and access thereto, a desiccant component mounted in the housing and substantially dividing the chamber into first and second regions, a support in the chamber for supporting at least one item within the first region, one or more passages interconnecting the first and second regions for providing a gas flow circulation path therethrough, the circulation path being (a) gas flow into contact with and through the desiccant component, (b) then into and thru the first region for contact with the item, (c) then thru the passage into the second region, and (d) then again into contact with the desiccant component to continue the circulation, and a gas moving mechanism in the chamber for forcing and maintaining the gas flow circulation path.

21 Claims, 3 Drawing Sheets

HEARING AID DRYING APPLIANCE

BACKGROUND OF THE INVENTION

This invention concerns a drying appliance for demoisturizing small items which come into contact with an ear canal or the like, and particularly concerns moisture sensitive items such as hearing aids, custom molded plugs and hearing protectors, or for storing the same in a substantially dry environment, whereby the longevity of the item and its functionality are markedly enhanced, and/or its sterilization is effected, and particularly concerns such appliance which is readily transportable, self-contained, and especially adapted for maintaining the operability and sterile condition of moisture-sensitive hearing aids and other small and intricate electrical or electronic devices.

It is a common characteristic of electrical or electronic devices or items, particularly where electrical or electronic switching components, or miniaturized batteries or the like are involved, for the circuitry to become corroded, short circuited, chemically attacked, or otherwise rendered less effective or completely inoperable by contact of the item with moisture, either from the ambient atmosphere, accident or, as in the case of hearing aids, from contact also with the users moist body tissues and ambient humidity. Also, and of marked concern is the fact that external otitis (infection in the ear canal) is a common malady for hearing aid users. The insertion of a hearing aid or mold into the ear canal reduces the ability of air to circulate causing increased moisture in the canal and also produces ideal conditions for bacteria development. Many hearing air users utilize ear drops at night which dry the ear canal and tend to keep it acidic in order to prevent or reduce otitis. However, each day's insertion of a hearing aid or earmold can reintroduce old bacteria from the hearing aid or mold back into the ear canal.

DESCRIPTION OF THE PRIOR ART

Heretofore, storage units for small electrical items such as button type batteries, and solar powered hearing aids have been developed as exemplified in U.S. Pat. Nos. 5,129,546; 5,210,804; and Des. 333,385. While these units are no doubt useful for their intended purposes, they do not address the moisture problem and are not capable of functioning in a demoisturizing manner.

OBJECTS OF THE INVENTION

Objects, therefore, of the present invention are: to provide a means for demoisturizing moisture sensitive items, and for storing the same under dry conditions; to provide such means which is self-contained and easily transportable; to provide such means with structure which affords protection to the item against damage while not in use and which also affords a convenient and attractive storage facility therefor; to provide such means in a structural form which allows for easy assembly and maintenance thereof; and to provide such means in a miniaturized form whereby it can be easily carried in a handbag or the like.

SUMMARY OF THE INVENTION

These and other objects hereinafter becoming evident have been attained in accordance with the present invention through the discovery of demoisturizing appliance structure which, in its broad aspects, comprises housing means having removable cap means for providing substantially sealed chamber means and access thereto, desiccant means mounted in said chamber means, support means in a first region in said chamber means for supporting at least one moisture sensitive item Therein, and gas moving means in said chamber means for forcing and maintaining gas flow circulation in said chamber means and into contact with said desiccant means and said item, said circulation path comprising gas flow into contact with and through said desiccant means, then into and thru a first region whereby said item is contacted with at least partially desiccated air, then into and thru a second region, and then again into contact with said desiccant means to continue said circulation.

In certain preferred embodiments:

(a) heater means is mounted in said chamber means for assisting in the removal of moisture from said item, said desiccant means substantially divides said chamber means into first and second regions, said support means is positioned in said first region for supporting at least one said item therein, passage means is provided interconnecting said first and second regions for providing a gas flow circulation path therethrough, said circulation path comprising (a) gas flow into contact with and through said desiccant means, (b) then into and Thru said first region whereby said item is contacted with at least partially desiccant air, (c) then thru said passage means into said second region, and (d) then again into contact with said desiccant means to continue said circulation.

(b) said gas moving means comprises fan means mounted upstream of said desiccant means, and wherein heater means is mounted between said desiccant means and said fan means, said fan means, desiccant means and heater means all being within said circulation path;

(c) said desiccant means and its mounting provide a substantially closed path for passage of circulating heated gas into said first region;

(d) said support means comprises flexible net means having a contact area of less than about 10% of the area of said item which is in contact with said surface means;

(e) said support means is laterally displaced from said passage means whereby substantially all of the circulating gas moves into close proximity to said item;

(f) said desiccant means is removably mounted in said housing means such that it can be readily replaced when its desired desiccating capacity is depleted;

(g) locator means is provided on interior portions of said housing means for functioning in cooperation with said heater means, desiccant means and support means to locate said heater means, desiccant means and support means in operative position within said housing means;

(h) said support means is located within said first region for supporting said item therein; and (i) U.V. sterilizing or germicidal lamp means is provided within the circulation path; and (j) any or all of the various components, e.g., item support means, desiccant means or heater means are in the form of drawer means which can be easily slid in or out of the chamber means through as side of the housing means.

The aforedescribed appliance provides an attractive storage space for hearing aids that are not in use while providing a drying and sterilizing environment for reducing or eliminating moisture and, at the same time, sterilizing the hearing aid, earmold or the like item. The dry environment also dries cerumen (ear wax) which is often attached to the item making its removal therefrom much easier. This appliance consists of a closed chamber with a miniature fan circulating heated air which is passed directly over the hearing aids. Situated within the chamber is a desiccant which absorbs moisture, which desiccant is easily removed when saturated and may be dried at a higher temperature such as in an oven, and reused in the dryer repeatedly. The chamber also preferably contains a germicidal lamp which may be directed into the air path or directly onto the hearing aid(s) or other item, thereby sterilizing the surface of the item as well as the circulated air. This chamber also preferably contains a heating element and thermostat for maintaining a constant temperature ideal for drying. An on/off switch and an indicator lamp for all electrically operated components is also included. A special drawer may be provided for convenient insertion and removal of the item as well as replacement of the desiccant.

BRIEF DESCRIPTION OF THE DRAWINGS

The invention will be further understood from the drawings herein of certain preferred embodiments, and the following description thereof, wherein.

DESCRIPTION OF THE PREFERRED EMBODIMENTS

Figure 1:
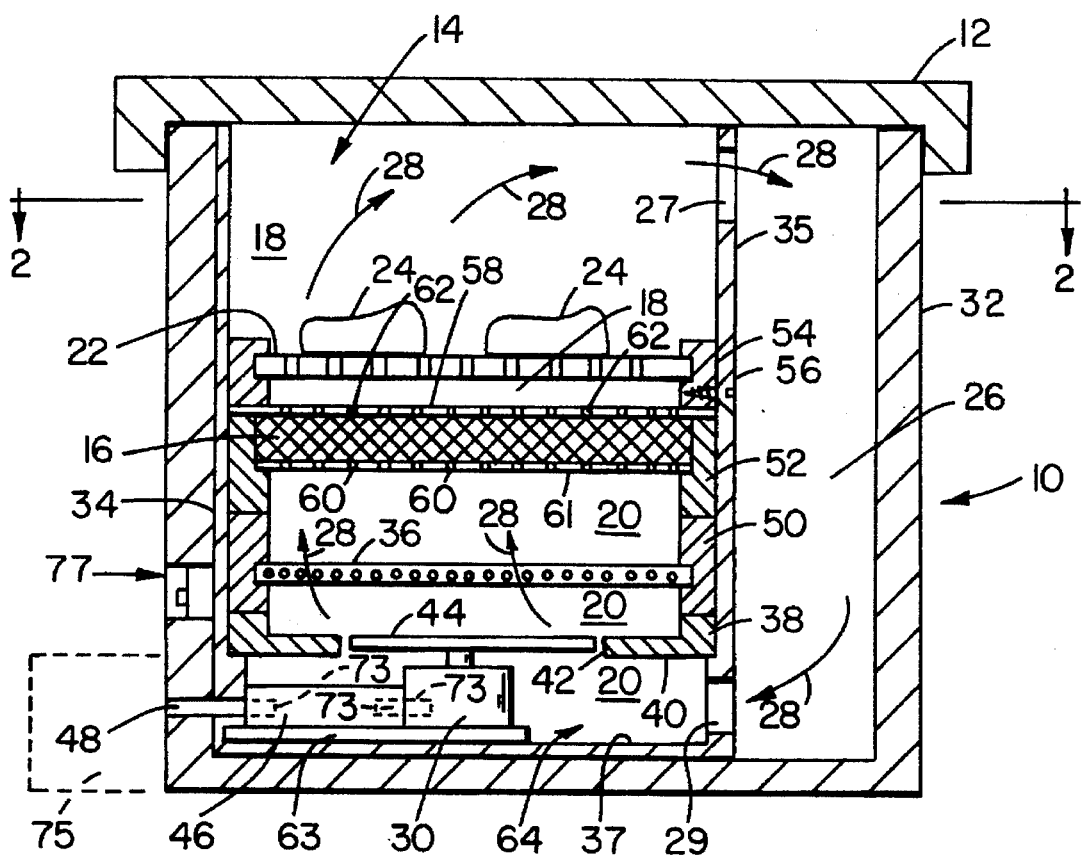
FIG. 1 is a longitudinal, vertical, cross-sectional view of the appliance.

Referring to the drawings, and with particular reference to the claims hereof, the present housing means generally designated 10 having removable cap means 12 for providing substantially sealed chamber means 14 and access thereto, desiccant means 16 such as CaO, $CaCl_2$, $ZnCl_2$, $CuSO_4$, or the like mounted in said housing means and substantially dividing said chamber means into first 18 and second 20 regions, support means 22 in said chamber means for supporting at least one said item 24 within said first region, one or more passage means 26 spaced around said chamber means and interconnecting said first and second regions thru openings 27 and 29 for providing a gas, e.g., air flow circulation path 28 therethrough, said circulation path comprising (a) gas flow into contact with and through said desiccant means 16, (b) then into and thru said first region 18 for contact with said item, (c) then thru said passage means 26 into said second region 20, and (d) then again into contact with said desiccant means 16 to continue said circulation, and gas moving or fan means 30 in said chamber means for forcing and maintaining said gas flow circulation path 28.

Figure 2:
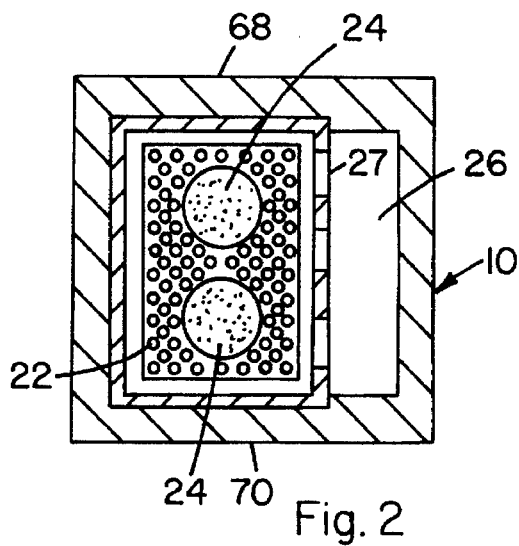
FIG. 2 is a lateral cross-sectional view taken along line 2—2 of FIG. 1 in the direction of the arrows.
Figure 6:
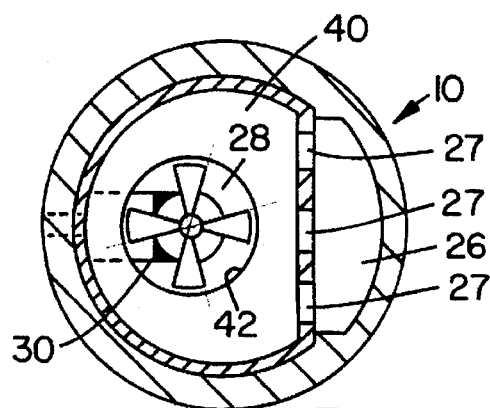
FIG. 6 is a view as in FIG. 2 with the item support, desiccant means, and heater means removed for clarity, and with the housing means configured generally circular in cross-section.

The housing means can be of any configuration and material, for example, with a lateral cross-sectional shape of square, rectangular, oval or round and of plastic, wood, ceramic or metal. As shown in FIGS. 1, 2 and 6, the housing may consist of outer section 32 and inner section 34 which, preferably, is in the general form of a removable cup 35. Mounted in the cup, or if only section 32 is employed, mounted on the inner wall portions thereof, are the components 22, 16 and 30, and also a miniature heater means such as electrical, grid heater 36. Cap 12 may be threaded onto the housing or dimensioned to provide a friction fit which allows its removal by simple twisting and pulling force.

In the construction shown, the cup sides are provided with shoulder means 38 on which baffle plate 40 rests and provides thru its opening 42 a portion of circulation path 28. The blade 44 of fan 30 preferably is mounted closely adjacent opening 42 such that its air moving efficiency is maximized and back flow is minimized.

Figure 11:
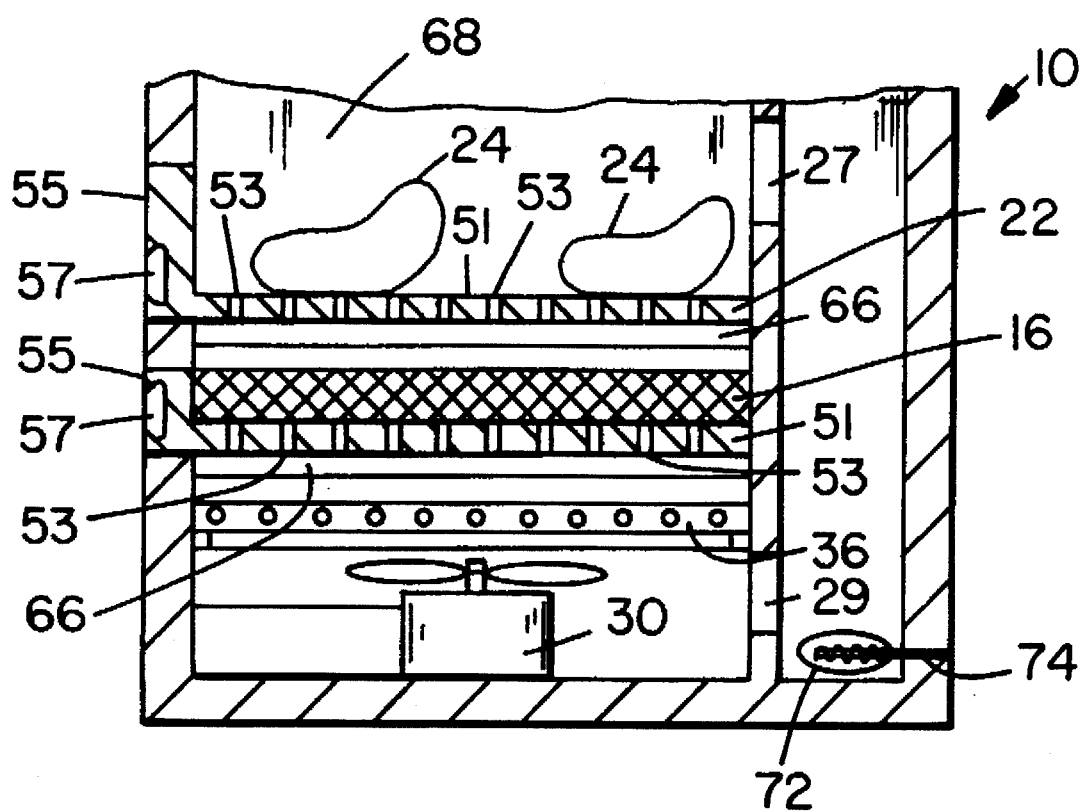
FIG. 11 is a view as in FIGS. 1 and 2 showing a variation in the mounting, i.e., a drawer type mounting, for the components of the appliance.

In the embodiment of FIG. 11 which illustrates the drawer type mounting for the various components of the appliance, each drawer, as illustrated for the item support means 22 and the desiccant means 16 comprises a floor means 51 having an adequate number of apertures 53 therethrough for proper drying air flow, and preferably having a front piece 55 with recesses 57 formed therein for being finger gripped for pulling the drawers out of the chamber. The floor means are slidably supported by rail means 66 affixed to the inner surfaces of opposite sides 68, 70 of the housing means.

It is noted that such structural features are important to the preferred embodiments of the present invention in that the miniature sizes and powers of the components employed require conservative engineering to be efficient in the very limited spaces available for them. In this regard, a useful set of operating parameters for an electrically operated fan 30 and heater 36 are that the fan motor and the heater preferably can operate from a three to six volt battery for about 30 minutes, with an airflow of from about 10 to about 50 cu.in./min., and a heat output of from about 0.5 to about 5.0 calories/min. Such warmed, desiccated air flow generally will satisfactorily dry a moist electronic item. Thereafter, the battery 46 can be recharged by any known and suitably reduced voltage power means thru electrical prong and socket access port 48. The aforesaid operating parameters can, of course, be widely varied as also may the type and power consumption and output energies of the fan and heater and the voltage and operating life of their power supply.

It is particularly noted that the type of heater which may be employed includes the chemical heater pack type which can be activated when desired and placed within the lower cavity 64. Such heating packs are typified by boot type warmers typically employing iron powder, water, vermiculite, activated charcoal and salts which, when exposed to oxygen within the contained package will chemically react and stay warm, e.g., about 100° F. to about 105° F., for several hours. For such a heating means, access port 48 may comprise a laterally elongated slot provided with a suitable cover whereby the chemical pack can be inserted into and removed from cavity 64.

In the embodiment shown, each component 36, 16, and 22 is provided with its own peripherally surrounding base means 50, 52 and 54 respectively which can be readily slid down into and stacked into cup 35. One or more screws such as 56 or other fastening means may be provided to fix base 54 to the cup side to thereby maintain the relative positions of all of the said components within the housing. It is noted that the support component 22 can actually be part of the top 58 of the desiccant means 16 within the scope of the terminology of the broad claims herein, in which case, screw 56 could be used alternatively in conjunction with base means 52. With such a stacking arrangement within cup 35, all of the components are rendered readily accessible for replacement or repair, e.g., replacement of the desiccant material simply by sliding the cup out of the outer section 32, removing screw 56 and then lifting the components out of the cup. In this regard, the desiccant material is preferably carried in a module shell 59 comprising bottom plate 61 and top plate 58 having a sufficient number of inlet apertures 60 and outlet apertures 62 respectively to allow proper flow of recirculating air thru the desiccant.

Figure 7:
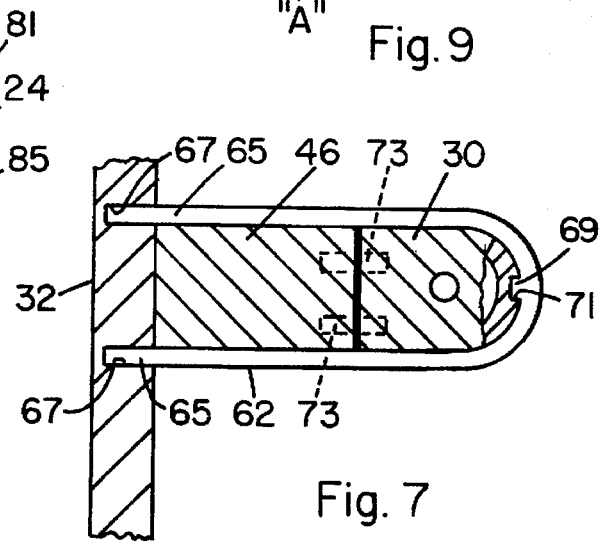
FIG. 7 is a view taken along line 7—7 of FIG. 1 in the direction of the arrows.
Figure 8:
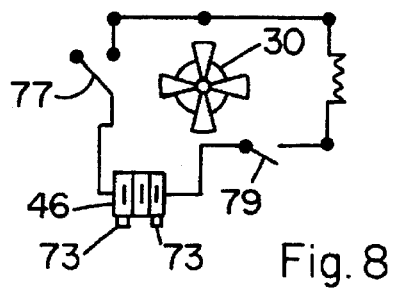
FIG. 8 is a schematic of an electrical circuit useful in the present appliance.

Referring to FIGS. 7 and 8, the battery 46 and motor 30 may be attached to each other in any suitable manner and affixed in position on the floor 37 of cup 35 by a strong and essentially inflexible bracket or clip 63, the ends 65 of which are pushed into tight fitting recesses 67 in the wall of section 32, and the nib 69 of which is inserted into recess 71 in the motor shell. With this construction, or with any equivalent construction, the motor and battery can be conveniently secured, but removably so, at a proper position in the appliance.

Figure 9:
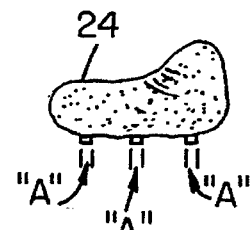
FIG. 9 is a side view of an item supported on a net, the cords of which are shown in cross-section in order to show the area "A" referred to herein.

A useful electrical circuit is shown schematically in FIG. 9 and in enlarged FIG. 8 wherein the connection of the battery to the motor, and of the battery to a charging unit 75 is made by plug in type connectors 73, and a push type, on/off switch 77 is mounted in wall 32, preferably flush with or inset from the outer surface of said wall for avoiding inopportune activation of the appliance during travel or the like. If desired, a second such switch 79 may be provided for the heater circuit such that the air circulation can proceed independently of heating the air. For extended periods of residency of the item in the appliance, this feature is very advantageous. It is noted that in situations where electrical power is available, the charging unit 75 and battery 30 may be replaced by a transformer device such that, e.g., normal house current may be used, in reduced voltage, to power the motor and heater. In this regard, the fan motor and electrical heater may be constructed to operate on house electrical power, e.g., 110 V, where, e.g., use of the appliance is to be only where such power is available.

The gas flow or circulation path 28 is initiated and maintained by gas moving means comprising either or both of fan 30 or heater 36. Where the residence time of the hearing aid in the appliance is, e.g., overnight, then the heater by itself will effect sufficient air flow upwardly thru the desiccant and cause sufficient air recirculation to subject the hearing aid to a continuously and sufficiently demoisturized gas flow to demoisturize the same. The obviously preferred gas is, of course air, however, for certain items which, e.g., may be prone to oxidation, a gas such as Helium may be injected by suitable means into the capped chamber and the air flushed therefrom and then resealed, whereby the Helium acts as the moisture pick-up medium.

A germicidal means such as a U.V. lamp 72 is preferably provided in any portion of the chamber means for purifying the recirculating air and the item. Suitable battery or house current electrical contact means 74 may extend through the housing wall for plug-in type electrical connection. Such useful germicidal lamps and their specifications are described in the 16 page General Electric, Large Lamp Department publication, TP-122, October, 1970.

Figure 4:
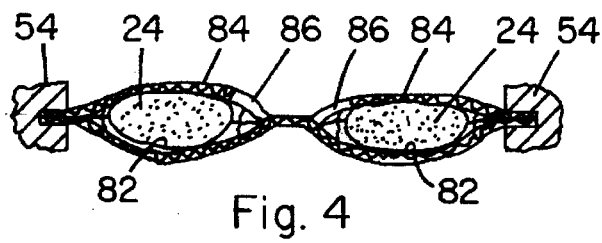
FIG. 4 is a cross-sectional view taken along line 4—4 of FIG. 3 in the direction of the arrows.
Figure 3:
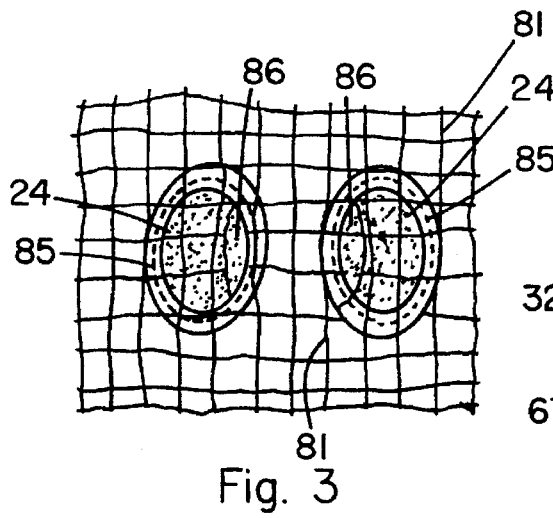
FIG. 3 is a top view of a preferred net form embodiment of the item support means.
Figure 5:
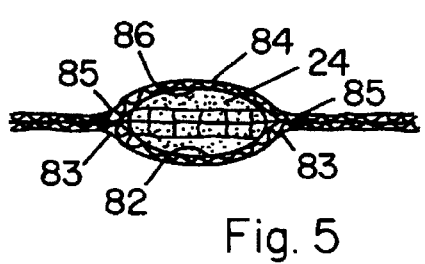
FIG. 5 is a view taken along line 5—5 of FIG. 4 in the direction of the arrows.

The net form construction 80 of the item support means as shown in FIGS. 3-5 may be of any natural or synthetic material, but preferably of fine denier cotton, silk, rayon or the like. This construction insures that the item will be essentially totally exposed to dried air flow since the netting covers only a minuscule surface area of the item. In this regard, such a small contact area, e.g., less than about 10% and preferably less than about 2% or less of the total area of the item which is substantially laterally covered by the cord 81 of the support means, and the nearly complete lack of mass of the netting cords, eliminates any formation of hot spots which might otherwise and damage the same. The said total area is the aggregate of the areas "A" of the contacting cords which may be of dimensions and strengths such as that of heavy duty sewing thread. In a preferred form of the net, one or more pocket means generally designated 82 are formed therein, e.g., by stitching around the periphery of the pocket as at 83 or hot forming of, e.g., the polyester or Nylon thread, to receive the item, and preferably are provided with a cover portion 84 stitched or adhesively secured as at 85 around the pocket means and shaped to provide an access opening 86 through which the item can be passed. It is noted that the net type of construction for the pocket means 82 and cover portion 84 readily allows the netting to be flexibly expanded around the opening 86 for facilitating entry and removal of the item into and from the pocket and then closing slightly to secure the item therein. It is noted that this net type of support provides considerable anti-shock safety for the item should the appliance be jostled about when being transported, or knocked from a night table, or the like.

Figure 10:
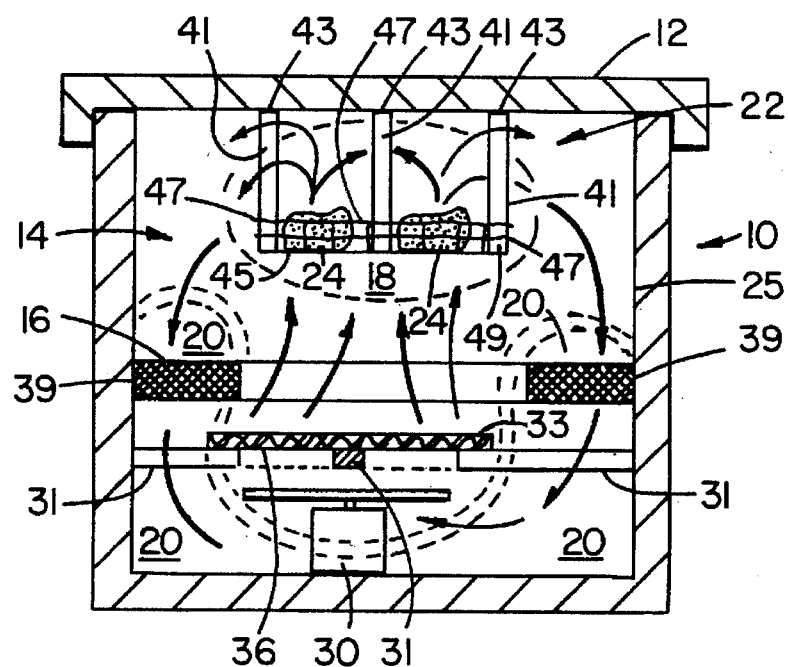
FIG. 10 is a cross-sectional view as in FIG. 1 somewhat reduced in size and showing a different arrangement of the various components of the appliance.

Referring to FIG. 10 wherein the identical or equivalent structures of FIG. 1 are numbered the same, and with particular reference to claim 23 hereof, the demoisturizing appliance comprises housing means 10 having removable cap means 12 for providing substantially sealed chamber means 14 and access thereto, desiccant means 16 mounted in said chamber means, support means 22 in a first region 18 in said chamber means for supporting at least one moisture sensitive item 24 therein, and gas moving means 30 in said chamber means for forcing and maintaining gas flow circulation in said chamber means and into contact with said desiccant means and said item, said circulation path comprising gas flow into contact with and through said desiccant means, then into and thru a first region 18 whereby said item is contacted with at least partially desiccated air, then into and thru a second region 20, and then again into contact with said desiccant means to continue said circulation.

In this embodiment, the grid heater 36, if a heater is to be employed, is supported by a plurality of members such as 31 which are secured at one end to the housing inner wall 25 and extend in a spider fashion radially inwardly to provide support end portions 33 for the heater. The desiccant means 16 may be of annular configuration with its radially outer periphery 39 affixed to wall 25, or the desiccant means may comprises, e.g., a plurality of arc-like segments affixed to wall 25. Referring to the embodiment of support means 22 of FIG. 10, a plurality, e.g., four circumferentially spaced hanger members 41 are affixed at their upper ends 43 to cap 12 and are secured at their lower ends 49 by adhesive or other means to a basket shaped net 45, the sides 47 of which extend upwardly a selected and sufficient distance to retain the items to the extent desired while allowing easy finger access thereto for entry into and removal from the support.

It is noted that region 18 is shown generally by single outline, and region 20 is shown generally by double outline. These regions are, of course, variable in scope, configuration, and location within said chamber means and within the context of the present invention, as are the particular locations and dimensions of the various components.

The invention has been described in detail with particular reference to preferred embodiments thereof, but it will be understood that variations and modifications will be effected with the spirit and scope of the invention.

I claim:

1. A hearing aid storage and conditioner appliance for demoisturizing and sanitizing a moisture sensitive item such as an electronic hearing aid or the like, comprising housing means having removable cap means for providing substantially sealed chamber means and access thereto, desiccant means mounted in said chamber means, support means in said chamber means, at least one of said desiccant means or said support means substantially dividing said chamber means into first and second regions, said support means supporting at least one said item within said first region, passage means interconnecting said first and second regions for providing a gas flow circulation path therethrough, said circulation path comprising (a) gas flow into contact with and through said desiccant means, (b) then into and thru said first region for contact with said item, (c) then thru said passage means into said second region, and (d) then again into contact with said desiccant means to continue said circulation, and gas moving means in said chamber means for forcing and maintaining said gas flow circulation path, wherein heater means is mounted in said chamber means for assisting in the removal of moisture from said item, said heater means being positioned in a lower portion of said circulation path, and germicidal lamp means mounted in said chamber means for chemically sanitizing said item.

2. The appliance of claim 1 wherein said heater means is mounted in said second region.

3. The appliance of claim 2 wherein said gas moving means comprises fan means mounted upstream of said desiccant means, and wherein said heater means is mounted between said desiccant means and said fan means, said fan means, desiccant means and heater means all being within said circulation path.

4. The appliance of claim 3 wherein said desiccant means and its mounting provide a substantially closed path for passage of circulating heated gas into said first region.

5. The appliance of claim 4 wherein said support means comprises substantially rigid plate means having a plurality of apertures therethrough.

6. The appliance of claim 4 wherein said support means comprises flexible net means.

7. The appliance of claim 1 wherein said support means is provided with surface means for engaging said item, said surface means having a contact area of less than about 10% of the area of said item which is in contact with said surface means.

8. The appliance of claim 7 wherein said support means is of flexible net construction.

9. The appliance of claim 8 wherein at least one pocket means is provided in said support means and adapted to receive and support an electronic hearing aid.

10. The appliance of claim 9 wherein said contact area is less than about 5% of the area of said hearing aid which is in contact with said surface means.

11. The appliance of claim 1 wherein said support means is laterally displaced from said passage means whereby substantially all of the circulating gas moves into close proximity to said item.

12. The appliance of claim 1 wherein said desiccant means is removably mounted in said housing means by pull-out drawer means such that it can be readily exposed to the user by simple finger manipulation.

13. The appliance of claim 3 wherein mounting means for each of said fan means, desiccant means and heater means are provided in said housing and delimit said recirculation path such that the gas must move essentially first through said fan means, then said hearer means and then through said desiccant means on its way to said support means and the item supported thereby.

14. The appliance of claim 1 wherein said support means is affixed to said cap means.

15. The appliance of claim 14 wherein said support means comprises net means.

16. The appliance of claim 1 wherein said support means comprises net means.

17. The appliance of claim 16 wherein pocket means are formed in said net means for receiving said item.

18. The appliance of claim 4 wherein locator means is provided on interior portions of said housing means for functioning in cooperation with said heater means, desiccant means and support means to locate said heater means, desiccant means and support means in operative position within said housing means.

19. The appliance of claim 1 wherein said support means comprises a surface portion of said desiccant means.

20. The appliance of claim 10 wherein said pocket means is substantially closed and is provided with a substantially laterally oriented access opening for insertion and removal of said hearing aid.

21. The appliance of claim 1 wherein said heater means functions also as said gas moving means.

* * * * *